(12) United States Patent
Truschel et al.

(10) Patent No.: US 8,714,152 B2
(45) Date of Patent: May 6, 2014

(54) VENTILATOR WITH LIMP MODE

(75) Inventors: William A. Truschel, Oakmont, PA (US); Andrew L. Shissler, Delmont, PA (US); Winslow K. Duff, Export, PA (US); Mark C. McDermott, Pittsburgh, PA (US); Michael H. Kissel, Harrison City, PA (US)

(73) Assignee: Koninklijke Philips N.V., Eindhoven (NL)

( * ) Notice: Subject to any disclaimer, the term of this patent is extended or adjusted under 35 U.S.C. 154(b) by 230 days.

(21) Appl. No.: 13/123,970

(22) PCT Filed: Oct. 9, 2009

(86) PCT No.: PCT/IB2009/054451
§ 371 (c)(1),
(2), (4) Date: Apr. 13, 2011

(87) PCT Pub. No.: WO2010/044035
PCT Pub. Date: Apr. 22, 2010

(65) Prior Publication Data
US 2011/0209706 A1 Sep. 1, 2011

Related U.S. Application Data

(60) Provisional application No. 61/105,876, filed on Oct. 16, 2008.

(51) Int. Cl.
*A61M 16/00* (2006.01)
(52) U.S. Cl.
USPC ............ 128/204.21; 128/204.18; 128/204.23; 128/204.26
(58) Field of Classification Search
USPC .............. 128/204.18, 204.21, 204.23, 204.26
See application file for complete search history.

(56) References Cited

U.S. PATENT DOCUMENTS

| 5,107,831 | A | | 4/1992 | Halpern | |
|---|---|---|---|---|---|
| 5,503,146 | A | * | 4/1996 | Froehlich et al. | 128/204.23 |
| 6,000,396 | A | | 12/1999 | Melker | |
| 2001/0004894 | A1 | * | 6/2001 | Bourdon | 128/204.23 |
| 2006/0070624 | A1 | * | 4/2006 | Kane et al. | 128/204.23 |
| 2006/0107953 | A1 | * | 5/2006 | Truschel et al. | 128/204.18 |
| 2006/0137687 | A1 | * | 6/2006 | Colla et al. | 128/204.21 |
| 2006/0196508 | A1 | * | 9/2006 | Chalvignac | 128/204.23 |
| 2007/0051371 | A1 | * | 3/2007 | Sullivan et al. | 128/206.22 |
| 2008/0000475 | A1 | | 1/2008 | Hill | |
| 2008/0053441 | A1 | | 3/2008 | Gottlib | |
| 2008/0295837 | A1 | * | 12/2008 | McCormick et al. | 128/204.21 |
| 2011/0197885 | A1 | * | 8/2011 | Wondka et al. | 128/204.22 |
| 2011/0214673 | A1 | * | 9/2011 | Masionis | 128/205.13 |

FOREIGN PATENT DOCUMENTS

EP 1205203 A2 5/2002

* cited by examiner

*Primary Examiner* — Clinton T Ostrup
*Assistant Examiner* — LaToya M Louis
(74) *Attorney, Agent, or Firm* — Michael W. Haas

(57) ABSTRACT

A method of operating a ventilator that includes steps of (a) providing a specified ventilation therapy to a patient through a ventilator according to a specification; (b) determining and storing a backup parameter relating to the operation of the ventilator or the breathing of the patient during the step of providing the specified ventilation therapy; (c) determining that an alarm condition exists that indicates a problem with the ventilator that would prevent the ventilator from providing the specified ventilation therapy to the patient according to the specification; and (d) responsive to determining that the alarm condition exists, providing backup ventilation therapy to the patient through the ventilator that is based at least partially on the stored backup parameter. Also, a ventilator that is adapted to perform the method just described.

Figure 1:
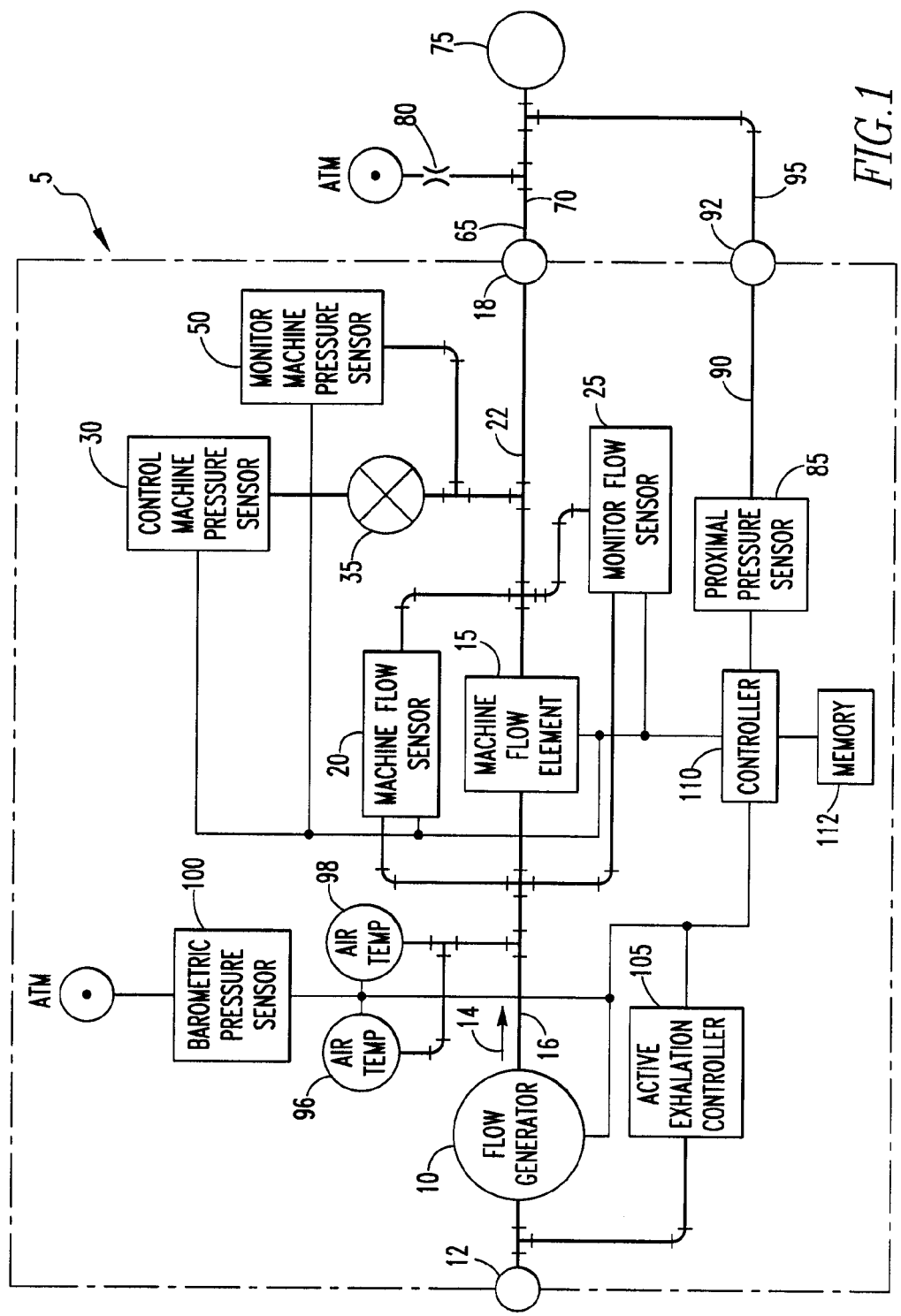

14 Claims, 5 Drawing Sheets

VENTILATOR WITH LIMP MODE

This patent application claims the priority benefit under 35 U.S.C. §119(e) of U.S. Provisional Application No. 61/105,876 filed on Oct. 16, 2008, the contents of which are herein incorporated by reference.

The present invention relates to a medical ventilator, and, in particular, to a medical ventilator that is adapted to provide backup therapy upon the detection a hardware problem within the ventilator that would otherwise prevent the ventilator from providing therapy to the intended specification.

A medical ventilator is a machine that is structured to deliver a gas, such as air, oxygen, or a combination thereof, to an airway of patient to augment or substitute for the patient's own respiratory effort. In addition, it is known to operate a conventional medical ventilator in a variety of modes depending upon the particular needs of the patient.

In a life support situation, where there is substantially no spontaneous respiratory effort by the patient, a controlled mode of ventilation is typically provided, where the ventilator assumes full responsibility for ventilating the patient. In this mode of ventilation, a controlled volume of gas is delivered to the patient during each inspiratory phase of the ventilatory cycle, and the trigger point (the transition from the expiratory phase to the inspiratory phase of the ventilatory cycle) and cycle point (the transition from the inspiratory phase to the expiratory phase of the ventilatory cycle) of the ventilator are typically determined based on time. Traditionally, ventilators used in life support situations employ what is known as a dual-limb patient circuit having an inspiratory limb for transporting gas to the patient and an expiratory limb for transporting gas from the patient to an exhaust assembly that includes a selectively controllable valve or similar mechanism for actively controlling the exhaustion of the patient's expired gas to atmosphere (referred to as "active exhaust").

In non-life support situations, where the patient exhibits some degree of spontaneous respiratory effort, an assist mode or a support mode of ventilation is typically provided in which the ventilator augments or assists in the patient's own respiratory efforts, typically by providing a predetermined pressure to the airway of the patient. In this mode of ventilation, the pressure of the flow of gas is controlled. For example, in bi-level non-invasive ventilation, an inspiratory positive airway pressure (IPAP) is delivered to the patient during the inspiratory phase of each ventilatory cycle, and an expiratory positive airway pressure (EPAP), which is typically lower than the IPAP level, is delivered to the patient during the expiratory phase of each ventilatory cycle.

Ventilators used in non-life support situations typically employ what is known as single-limb patient circuit having only one limb that is used for transporting gas both to and from the patient. In addition, such single-limb patient circuits normally include an exhaust port, often in the form of a hole in the limb or the patient interface, to allow the patient's expired gas to be passively vented to atmosphere (referred to as "passive exhaust").

In current ventilators (both those used in life support situations and those used in non-life support situations), when a hardware problem arises with the ventilator that would prevent the ventilator from providing therapy to the patient according to the desired specification for that therapy, the ventilator is caused to shut down and sound various alarms for alerting the patient's caregiver of the problem. As will be appreciated, this can be dangerous, in particular in the case of a ventilator used in a life support situation, because the patent's caregiver may not always be nearby to remedy the problem. There is, therefore, room for improvement in medical ventilators and in methods associated with the same.

Accordingly, it is an object of the present invention to provide a ventilator that overcomes the shortcomings of conventional ventilator. This object is achieved according to one embodiment of the present invention by providing a method of operating a ventilator that includes steps of (a) providing a specified ventilation therapy to a patient through a ventilator according to a specification; (b) determining and storing a backup parameter relating to the operation of the ventilator or the breathing of the patient during the step of providing the specified ventilation therapy; (c) determining that an alarm condition exists that indicates a problem with the ventilator that would prevent the ventilator from providing the specified ventilation therapy to the patient according to the specification; and (d) responsive to determining that the alarm condition exists, providing backup ventilation therapy to the patient through the ventilator that is based at least partially on the stored backup parameter.

The step of determining and storing the backup parameter may include calculating an average of an operational parameter of the ventilator or a breathing parameter of the patient over a predetermined number of breaths taken by the patient during step (a). Specifically, the backup parameter may include one or more of (1) an average generator speed during IPAP delivery over the predetermined number of breaths, (2) an average generator speed during EPAP delivery over the predetermined number of breaths, (3) an average IPAP level delivered to the patient over the predetermined number of breaths, (4) an average EPAP level delivered to the patient over the predetermined number of breaths, (5) a patient breath rate average over the predetermined number of breaths, and (6) a patient inspiration time average over the predetermined number of breaths.

In another particular embodiment, the method further includes determining whether each of the predetermined number of breaths is a valid breath. In this embodiment, the step of determining and storing the backup parameter is performed only if each of the predetermined number of breaths is determined to be a valid breath. Also, the step of determining and storing the backup parameter may be repeated each time a new valid breath is taken by the patient such that the backup parameter is re-determined and re-stored for the most recent in time of the predetermined number of breaths.

Preferably, the alarm condition indicates a hardware problem with the ventilator that would prevent the ventilator from providing the specified ventilation therapy to the patient according to the specification. For example, the alarm condition may indicate a problem with a sensor or a problem with the patient circuit. Also, the present invention contemplates that the backup ventilation therapy is either (i) a flow generator speed type ventilation therapy that is based on the stored backup parameter, or (ii) a pressure support type ventilation therapy that is based on the stored backup parameter, and the particular type of backup therapy is determined based on the alarm type.

In another embodiment, the invention provides a ventilator that includes (a) a housing having an interior and an exterior; (b) an inlet port extending from the exterior to the interior of the housing; (c) a flow generator disposed within the ventilator and being structured to generate a flow of gas; (d) an outlet port for discharging the flow of gas from the housing; (d) a patient circuit in fluid communication with the outlet port and being structured to deliver the flow of gas to an airway of a patient during an inspiratory phase of a ventilatory cycle; and (f) a controller disposed in the housing and being operatively coupled to the flow generator. In this embodiment, the controller is adapted to implement one of more of the embodiments of the method just described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 2:
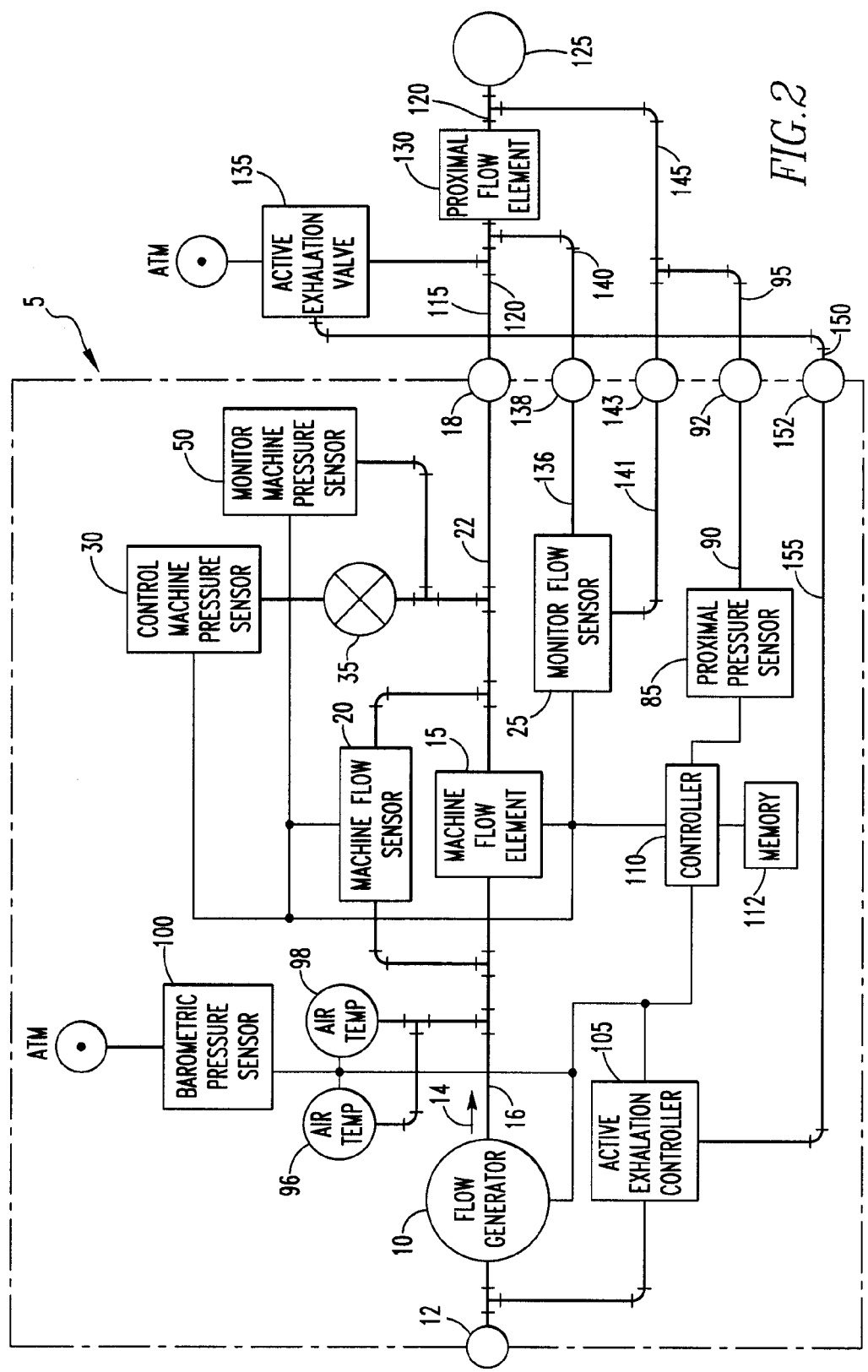
Figure 3:
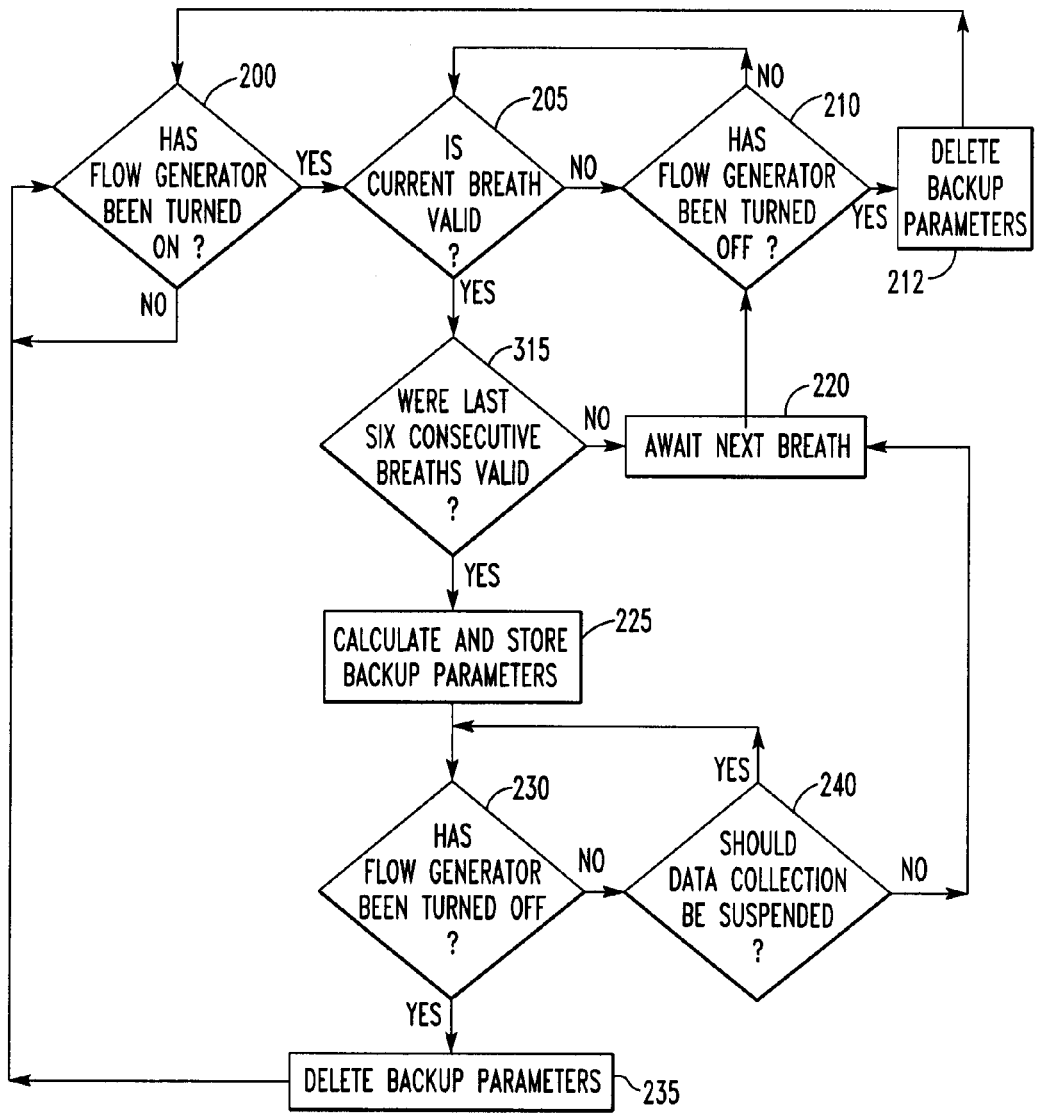
Figure 4A:
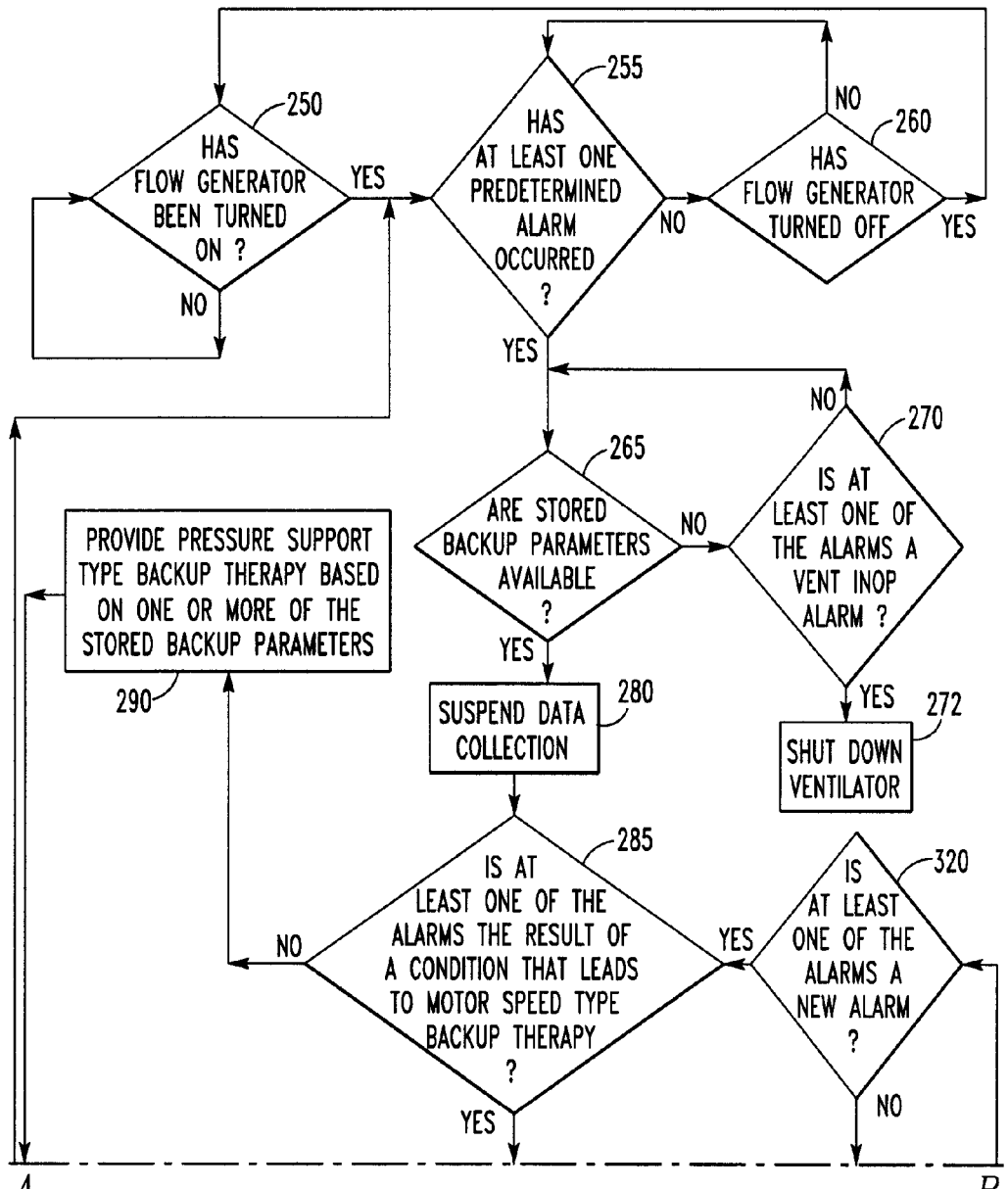
Figure 4B:
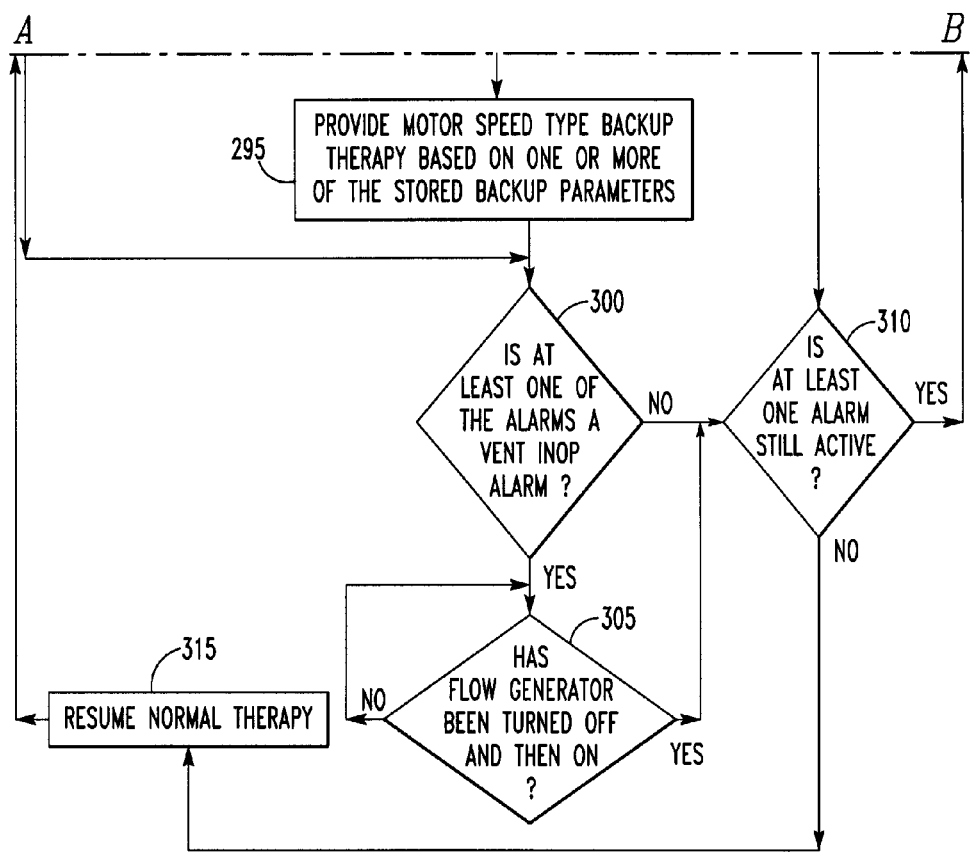

FIGS. 1 and 2 are schematic diagrams of an illustrative embodiment of a ventilator in which the present invention may be implemented;

FIGS. 3, 4A, and 4B are flowcharts illustrating various aspects of an embodiment of a method that may be implemented in a ventilator in order to provide backup therapy in the event of a hardware problem according to the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "patient interface" refers to any known or suitable mechanism for transporting gas to and from the airway of a patient and expressly includes, but is not limited to, non-invasive patient interfaces such as masks, nasal canulas, combination nasal/oral masks and removable mouth pieces, and invasive patient interfaces such as tracheal tubes and endotracheal tubes, as well as humidifiers, nebulizers and meter dose inhalers, which can be invasive or non-invasive.

As employed herein, the term "mode" refers to the operation of the ventilator for providing a particular type of ventilation therapy, expressly including but not limited to, pressure support ventilation therapy, volume control ventilation therapy and suitable combinations thereof. Each mode may have one or more attributes such as, for example and without limitation, CPAP, SMIE, S, S/T, AC, PC, PC-SIMV, or CV.

As employed herein, the statement that two or more parts or components are "coupled" together shall mean that the parts are joined or operate together either directly or through one or more intermediate parts or components.

As employed herein, the term "number" shall mean one or an integer greater than one (i.e., a plurality).

The present invention provides a method that enables a medical ventilator to provide continued, backup therapy to a patient when a hardware problem in the ventilator is detected that would otherwise prevent the ventilator from providing therapy to the patient according to a specification (e.g., a specification prescribed by a physician or other caregiver). In other words, if the ventilator fails to operate properly, depending on the type of failure, the ventilator will attempt to continue to deliver a therapy that is close to that which would have been provided but for the failure. This mode of operating the ventilator in the best possible way following a failure is sometimes referred to as a "limp mode" because this ventilator will attempt to "limp" along rather than stop altogether in the event of certain failures or partial failures.

FIGS. 1 and 2 are schematic diagrams of an illustrative embodiment of a particular ventilator 5 in which the present invention may be implemented. As described in greater detail below, ventilator 5 shown in FIGS. 1 and 2 is capable of being selectively configured to provide ventilation to a patient in a number of different modes, including volume controlled and pressure support modes (with particular attributes), using either passive or active exhaust and a single-limb patient circuit.

It should be understood, however, that the ventilator 5 shown in FIGS. 1 and 2 and described in greater detail below is being used for illustrative purposes only in order to describe an implementation of the method of the present invention, and that the method described herein may be implemented in other types of ventilators having various other capabilities and modes of operation. Ventilator 5 should therefore not be considered to be limiting.

In FIG. 1, ventilator 5 is shown in a configuration in which passive exhaust is employed. Ventilator 5 includes within a housing a flow generator 10 adapted to generate a flow of gas, such as air from an ambient air inlet port 12 (extending from the exterior to the interior of the housing) and/or a mixture of air and oxygen provided from the ambient air inlet port 12 and an optional oxygen source (not shown). Flow generator 10 may be any device suitable for creating a flow of gas (indicated by the arrow 14) at a pressure greater than ambient atmosphere, such as a compressor, fan, impeller, blower, piston or bellows. In an exemplary embodiment, flow generator 10 is a micro-turbine comprising a blower assembly having a brushless DC motor with an impeller designed to generate the pressures and flows required by the ventilator. Flow generator 10 is in fluid communication with a machine flow element 15 through a conduit 16. Machine flow element 15 is a mechanical element positioned at or about the outlet of flow generator 10 that is designed to produce a pressure drop when flow passes through it. As seen in FIG. 1, machine flow element 15 is in fluid communication with an outlet port 18 of ventilator 5 through a conduit 22.

A machine flow sensor 20 is provided in tandem with machine flow element 15 to measure the volumetric flow of the flow of gas passing through the flow element, which, for the most part is the flow of gas created by flow generator 10. In the illustrated exemplary embodiment, a monitor flow sensor 25 is also provided in tandem with machine flow element 15 to monitor the volumetric flow in a redundant manner. Preferably, one or both of machine flow sensor 20 and monitor flow sensor 25 is a differential pressure sensor. Furthermore, machine flow sensor 25 may be used in tandem with a proximal pressure sensor 85 (FIG. 2) to measure volumetric gas flow from the patient during exhalation and to provide improved triggering sensitivity and accuracy of the exhaled tidal volume. It can be appreciated that the ventilator need not have both flow sensors. In addition, the present invention even further contemplates eliminating both flow sensors in favor of measuring the flow rate, or a parameter indicative of the flow rate, using other techniques, such as based on the power provided to flow generator, the speed of the flow generator, etc.

A control machine pressure sensor 30 is operatively coupled to conduit 22 through an auto zero valve 35. In an exemplary embodiment, control machine pressure sensor 30 is a static pressure sensor and is used to monitor the pressure at outlet port 18 of ventilator 5. In addition, a monitor machine pressure sensor 50 is operatively coupled to conduit 22 and is also a static pressure sensor used to monitor the pressure at outlet port 18 of ventilator 5 in a redundant fashion. It can be appreciated that the ventilator need not have both pressure sensors.

As seen in FIG. 1, a single-limb patient circuit 65 is in fluid communication with the outlet port 18 of ventilator 5 and includes a conduit 70 and a patient connection port 75 adapted to the connected to a patient interface assembly, such as a mask, mouthpiece, combination nasal/oral mask, full face mask, tracheal tube, or endotracheal tube, for delivering the flow of gas to the airway of the patient. The single-limb patient circuit 65 in the embodiment shown in FIG. 1 includes a passive exhalation valve 80 for venting gas expired by the patient to the atmosphere. Furthermore, ventilator 5 in this embodiment includes a proximal pressure sensor 85 that is in fluid communication with the single-limb patient circuit 65 through internal conduit 90, port 92 and external conduit 95. In an exemplary embodiment, proximal pressure sensor 85 is a static pressure sensor used to measure delivered gas pressure at the patient connection port 75.

In addition, ventilator 5 includes temperature sensors 96 and 98 which are operatively coupled to the conduit 16 and are used to monitor the temperature of the gas exiting the flow generator 10. Also, a barometric pressure sensor 100 is provided for measuring atmospheric pressure to allow for altitude adjustment of calculated volumetric flow.

Although not employed in the configuration of ventilator 5 shown in FIG. 1, the ventilator includes an active exhalation controller 105 (described in more detail below) that is used when the ventilator is configured as shown in FIG. 2 to provide for active exhaust. Finally, ventilator 5 shown in FIG. 1 includes a controller 110 such as a microprocessor, a microcontroller, or some other suitable processing device, that is operatively coupled to a memory 112. Memory 112 can be any of a variety of types of internal and/or external storage media, such as, without limitation, RAM, ROM, EPROM(s), EEPROM(s), and the like, that provide a storage medium for data and software executable by the controller 110 for controlling the operation of ventilator 5 as described herein. As shown in FIG. 1, processor 110 is in electronic communication with certain of the other components shown in FIG. 1 in order to control such components and/or receive data from such components.

Referring to FIG. 2, ventilator 5 is shown in a single-limb configuration adapted for providing active exhaust. Thus, as seen in FIG. 2, ventilator 5 includes an alternate single-limb patient circuit 115 in fluid communication with outlet port 18. Single-limb patient circuit 115 includes a conduit 120, a patient connection port 125 similar to patient connection port 75, a proximal flow element 130, and an active exhalation valve 135. Proximal flow element 130 is a mechanical element positioned at or about patient connection port 125 that is designed to produce a pressure drop when flow passes through it. In an exemplary embodiment, active exhalation valve 135 is a proportionally controlled pressure relief valve in single-limb patient circuit 115 that provides for low resistance and includes carbon dioxide flushing during patient exhalation. In addition, active exhalation valve 135 provides for low exhalation resistance in the event of loss of therapy to meet anti-asphyxia requirements.

As seen in FIG. 2, in the configuration shown therein, monitor flow sensor 25 is operatively coupled to conduit 120 at either end of proximal flow element 130 rather than being operatively coupled to conduits 16 and 22 as in the configuration of FIG. 1. In particular, monitor flow sensor 25 is operatively coupled at or about a first end of proximal flow element 130 through an internal conduit 136, a port 138 and an external conduit 140, and at or about a second end of proximal flow element 130 through an internal conduit 141, a port 143 and an external conduit 145. Furthermore, active exhalation controller 105 in this configuration is operatively coupled to active exhalation valve 135 by way of an external conduit 150, a port 152 and an internal conduit 155.

Active exhalation controller 105 is a pressure control unit that, under the control of controller 110, regulates the pilot pressure of active exhalation valve 135 diaphragm in order to control bias flow during patient exhalation. Active exhalation controller 135 includes a dump valve to quickly reduce the pilot pressure from the diaphragm of active exhalation valve 135 to allow it to fully open at the beginning of exhalation. Active exhalation controller 105 also includes a proportional valve that is used in combination with an orifice provided between the two valves to control bias flow.

In still a further embodiment, the configuration of ventilator 5 shown in FIG. 1 may be altered so as to not include the operative coupling between proximal pressure sensor 85 and single-limb patient circuit 65. As will be appreciated, such a configuration would not include control based on measured proximal pressure.

Although not shown, the present invention contemplates that ventilator 5 includes an input/output component (e.g., user interface) or components. The input/output component is used, for example, for setting various parameters used by the ventilator as well as for displaying and outputting information and data to a user. The input/output component may be any device suitable to provide information and/or commands to controller 110 via an operative link and to present information to the patient, or another user, in a human perceivable format. Examples of a suitable input/output device includes a keypad, keyboard, touch pad, mouse, visual display (e.g., LCD or LED screen), microphone, speaker, switches, button, dials, lamps, or any other devices that allow a user to input information to and receive information from the ventilation system. The present invention further contemplates providing a wireless link as an input/output component to enable remote communication with the ventilator wirelessly.

FIGS. 3, 4A, and 4B are flowcharts illustrating various aspects of an embodiment of a method that may be implemented in ventilator 5 (in any of the configurations described herein) for enabling the ventilator to provide backup therapy upon the detection of a hardware problem within the ventilator that would prevent the ventilator from providing therapy to a patient according to an established specification. Again, as noted above, ventilator 5 (and its various configurations) is being used herein for illustrative purposes only, and it should be understood that the method described herein may be employed in other ventilator types and/or configurations and is not intended to be limited to use with the ventilator.

As described in further detail below, the method provides backup therapy to the patient when particular types of predetermined hardware problems have been detected that result in the generation of one or more alarms. The backup therapy is, in a non-limiting exemplary embodiment, in the form of either a motor speed (RPM) based therapy (wherein set flow generator speeds are used to provide the therapy) or a pressure support based therapy (wherein set pressure levels are used to provide the therapy), wherein each is based on certain calculated and stored backup parameters. For illustrative purposes, one particular embodiment of the method of the present invention is shown in FIGS. 3, 4A, and 4B. Specifically, FIG. 3 is a flowchart illustrating how, in that embodiment, the backup parameters are calculated and stored, and FIGS. 4A and 4B are a flowchart illustrating how, in that embodiment, the backup therapy is to be provided, if at all.

In the particular illustrative embodiment described in connection with FIGS. 3, 4A, and 4B, the following two types of alarms may be generated: (i) a ventilator inoperative (Vent Inop) alarm, which indicates that one or more hardware failures have occurred, and (ii) a circuit check alarm, which indicates the existence of a problem with the patient circuit, such as a situation where the type of patient circuit (passive or active) entered into the user interface of ventilator 5 does not match the actual patient circuit (single-limb patient circuit 65 (passive) or single-limb patient circuit 115 (active)) that is actually attached to the ventilator. In addition, this particular non-limiting embodiment contemplates eighteen specific predetermined alarms that may be generated. Table 1, provided below, includes a description of each of those eighteen alarms, the alarm type assigned to that alarm, and the type of backup therapy (motor speed (RPM) based or pressure support based) that is to be provided in the event of each alarm. Table 2 provided below provides a description of some of the possible causes or conditions that might lead to each alarm listed in Table 1

TABLE 1

| Alarm Description | Alarm Type | Backup Therapy Mode |
|---|---|---|
| Duel Pressure Sensor Failure | Vent Inop | Motor Speed |
| Blower Model Deviation Error | Vent Inop | Motor Speed |
| High Pressure Patient Alarm | Vent Inop | Motor Speed |
| Non-Volatile Memory Data Schema Failure | Vent Inop | Motor Speed |
| Non-Volatile Memory Data Checksum Failure | Vent Inop | Motor Speed |
| Non-Volatile Memory Data Readback Failure | Vent Inop | Motor Speed |
| Non-Volatile Memory Data Range Failure | Vent Inop | Motor Speed |
| Active Circuit Proximal Flow Patient Side Tube Failure | Circuit Check | Motor Speed |
| Active Circuit Proximal Flow Valve Side Tube Failure | Circuit Check | Motor Speed |
| Dual Flow Sensor Failure | Vent Inop | Pressure Support |
| Active Circuit Control Flow Sensor Failure | Vent Inop | Pressure Support |
| Active Circuit Proximal Flow Sensor Failure | Vent Inop | Pressure Support |
| Passive Circuit, UI Marked as Active | Circuit Check | Pressure Support |
| Active Circuit, UI Marked as Passive | Circuit Check | Pressure Support |
| Monitor/Proximal Flow Sensor Detection Problem | Circuit Check | Pressure Support |
| Large Leak In Circuit | Circuit Check | Pressure Support |
| Active Valve Control Problem | Circuit Check | Pressure Support |
| Control Flow Sensor Reads Low | Circuit Check | Pressure Support |

TABLE 2

| Alarm Description | Possible Cause(s) |
|---|---|
| Duel Pressure Sensor Failure | Analog-to-digital converter (ADC) failure, sensor board connector fails/falls off, both pressure sensors (30, 50) actually fail |
| Blower Model Deviation Error | In one embodiment, a software model of the speed of the flow generator 10 required for pressure generation is created; if the model number differs too much from the actual readings, this error is generated |
| High Pressure Patient Alarm | If the ventilator 5 attempts to provide more than a certain pressure, e.g., 60 cmH2O, this alarm is generated; can be due to circuit clamping or bad sensors |
| Non-Volatile Memory Data Schema Failure | Non-volatile data is the memory 112 is corrupted so that the ventilator 5 cannot tell what version of the data to use |
| Non-Volatile Memory Data Checksum Failure | Non-volatile data in the memory 112 is corrupted so that a data checksum fails |
| Non-Volatile Memory Data Readback Failure | An update to non-volatile data in the memory 112 did not occur successfully |
| Non-Volatile Memory Data Range Failure | Non-volatile data in the memory 112 is corrupted so that data is out of a permitted range |
| Active Circuit Proximal Flow Patient Side Tube Failure | A conduit comes off the active exhalation valve 135 such that flow or exhaled Vt cannot be measured accurately |
| Active Circuit Proximal Flow Valve Side Tube Failure | A conduit comes off the active exhalation valve 135 such that flow or exhaled Vt cannot be measured accurately |
| Dual Flow Sensor Failure | ADC failure, sensor board connector fails/falls off, both flow sensors (20, 25) actually fail |
| Active Circuit Control Flow Sensor Failure | Sensor inside the ventilator 5 used for flow control fails such that the ventilator 5 cannot accurately control delivered Vt |
| Active Circuit Proximal Flow Sensor Failure | Sensor inside the ventilator 5 used to measure exhaled Vt fails such that the ventilator 5 cannot accurately measure exhaled Vt |
| Passive Circuit, UI Marked as Active | Incorrect patient circuit set up, patient circuit (65, 115) changed without changing Circuit Type on user interface (UI) |
| Active Circuit, UI Marked as Passive | Incorrect patient circuit set up, patient circuit (65, 115) changed without changing Circuit Type on UI |
| Monitor/Proximal Flow Sensor Detection Problem | Unable to get readings from sensors because they are railed or out of range |
| Large Leak In Circuit | Mask came off patient or trach tube became dislodged |
| Active Valve Control | Active exhalation valve 135 not responding to software |

TABLE 2-continued

| Alarm Description | Possible Cause(s) |
| --- | --- |
| Problem | control requests because it is stuck or not installed correctly |
| Control Flow Sensor Reads Low | Control slow sensor 25 fails |

Referring to FIG. 3, the method of determining backup parameters is shown and begins at step 200, wherein a determination is made as to whether flow generator 10 has been turned on. If the answer is no, then the method returns to step 200 to await the activation of the flow generator. If, however, the answer at step 200 is yes, then, at step 205, a determination is made as to whether the current breath taken by the patient through ventilator 5 is valid. In one particular non-limiting embodiment, a breath is considered to be valid if none of the following conditions is present: (1) a Circuit Check type alarm, (2) an alarm indicating that the inspiration pressure is low (i.e., lower than some predetermined level), (3) an alarm indicating that the inspiration pressure is high (i.e., higher than some predetermined level), (4) an alarm indicating that the expiration pressure is low (i.e., lower than some predetermined level), or (5) an alarm indicating that the expiration pressure alarm is high (i.e., higher than some predetermined level). If the answer at step 205 is no, then, at step 210, a determination is made as to whether the flow generator has been turned off. If the answer is no, then the method returns to step 205 to determine whether the next breath is valid. If, however, the answer at step 210 is yes, then, at step 212, the backup parameters (described below), if any, currently stored in the memory 112 are deleted and the method returns to step 200.

If the answer at step 205 is yes, meaning that the current breath is valid, then, at step 215, a determination is made as to whether the last six consecutive breaths were also valid. If the answer at step 215 is no, then the method proceeds to step 220 where the method awaits the next breath and then proceeds to step 210. If, however, the answer at step 215 is yes, meaning that the last six consecutive breaths were valid, then, at step 225, controller 110 calculates and stores (in the memory 112) certain backup parameters relating to the past operation of ventilator 5 and/or the past breathing of the patient that are available to be used in the provision of backup therapy (FIGS. 4A and 4B) if appropriate.

In the particular embodiment being described, the backup parameters include the following six parameters: (1) an average flow generator speed during IPAP (inspiratory positive airway pressure) delivery over six breaths, (2) an average flow generator speed during EPAP (expiratory positive airway pressure) delivery over six breaths, (3) an average IPAP level delivered to the patient over six breaths, (4) an average EPAP level delivered to the patient over six breaths, (5) a patient breath rate average over six breaths, and (6) a patient inspiration time average over six breaths.

Following step 225, the method proceeds to step 230, wherein a determination is made as to whether flow generator 10 has been turned off. If the answer is yes, then, at step 235, the currently stored backup parameters are deleted and the method returns to step 200. If, however, the answer at step 230 is no, then, at step 240, a determination is made as to whether data collection for purposes of calculating backup parameters should be suspended (the basis for such a suspension is described below). If the answer is no, then the method returns to step 220. If the answer at step 240 is yes, then the method returns to step 230. In one particular embodiment, the occurrence of one or more of following conditions shall cause data collection for the calculation of backup parameters to be suspended: (1) a Circuit Check type alarm, (2) an alarm indicating that the inspiration pressure is low (i.e., lower than some predetermined level), (3) an alarm indicating that the inspiration pressure is high (i.e., higher than some predetermined level), (4) an alarm indicating that the expiration pressure is low (i.e., lower than some predetermined level), or (5) an alarm indicating that the expiration pressure alarm is high (i.e., higher than some predetermined level).

Thus, as will be appreciated from the above description, the method illustrated in FIG. 3 will result in backup parameters being calculated and stored for later use in providing backup therapy only if seven consecutive valid breaths have been provided following any instance of the flow generator 10 being turned on. In other words, backup parameters are calculated and stored only when a current breath is considered valid and the last six consecutive breaths were also valid. Furthermore, data collection will be suspended when it is determined that ventilator 5 is unstable, but has not degraded to the point of initiating backup therapy as described elsewhere herein. Once data collection has been suspended, the backup parameters are not recalculated and stored until seven consecutive valid breaths are detected. During the time that data collection is suspended, as will be appreciated from the description accompanying FIGS. 4A and 4B, if backup therapy is initiated, then the backup parameters saved before data collection was suspended are used as the control parameters in the provision of the backup therapy.

As noted elsewhere herein, FIGS. 4A and 4B are a flowchart illustrating how, in one particular embodiment, a backup therapy is to be provided to a patient. Referring to FIGS. 4A and 4B, the method begins at step 250, wherein a determination is made as to whether flow generator 10 has been turned on. If the answer is no, then the method returns to step 250 to await activation of the flow generator. If, however, the answer is yes, then, at step 255, a determination is made as to whether at least one predetermined alarm has occurred. In the particular embodiment being described, those alarms are set forth in Table 1 provided elsewhere herein. If the answer at step 255 is no, then, at step 260, a determination is made as to whether the flow generator has been turned off. If the answer is yes, then the method returns to step 250, and if the answer is no, then the method returns to step 255.

If, however, the answer at step 255 is yes, meaning that at least one predetermined alarm has occurred, then the method proceeds to step 265, wherein a determination is made as to whether stored backup parameters (see FIG. 3) are available. If the answer at step 265 is no, then, at step 270, a determination is made as to whether at least one of the alarms is a ventilator inoperative (Vent hop) alarm. The alarm type assigned to each of the particular predetermined alarms in the particular embodiment being described is set forth in Table 1. If the answer at step 270 is yes, meaning that at least one of the alarms is a ventilator inoperative (Vent Inop) alarm, then, at step 272, the ventilator is shut down and remains completely inoperative.

If, however, the answer at step 270 is no, meaning that each of the one or more alarms is a circuit check type alarm, then the method returns to step 265 to determine whether stored backup parameters have become available. As described elsewhere herein in connection with FIG. 3, stored backup parameters will only become available if seven consecutive valid breaths have been detected at least once between the flow generator 10 being turned on and the occurrence of an alarm. Thus, in short, if backup parameters are not yet available, the ventilator is shut down if one of the alarms is a ventilator inoperative (Vent Inop) alarm, and the ventilator awaits the storage of backup parameters if the alarms consist only of circuit check type alarms.

If, however, the answer at step 265 is yes, meaning that the stored backup parameters are available, then, at step 280, data collection for the purpose of calculating backup parameters is suspended. Next, at step 285, a determination is made as to whether at least one of the alarms is an alarm that will result in the provision of backup therapy based upon motor speed (RPM). Again, for the particular embodiment being described, Table 1 sets forth the type of backup therapy is to be provided in the case of each of the predetermined alarms. If the answer at step 285 is no, meaning that motor speed (RPM) backup therapy is not to be provided, but instead pressure support type backup therapy is to be provided, then the method proceeds to step 290.

As described elsewhere herein, in the event of either motor speed (RPM) or pressure support backup therapy, the actual therapy that is provided is determined based upon certain of the stored backup parameters. Thus, at step 290, where pressure support type backup therapy is to be provided, ventilator 5 is caused to provide the appropriate pressure support type backup therapy based upon the appropriate the stored backup parameter(s). In the particular embodiment being described, the average IPAP level delivered to the patient over six breaths is used to set the pressure level for the IPAP cycle and the average EPAP level delivered to the patient over six breaths is used to set the pressure level for the EPAP cycle. In addition, if appropriate for the current mode of the ventilator 5 (e.g., for S/T, T, PC, PC-SIMV, AC, CV and SIMV modes which are known in the art), the patient breath rate average over six breaths is used to determine how often IPAP/EPAP cycles are provided, and the patient inspiration time average over six breaths is used to set the breath length of the inspiratory phase.

If the answer at step 285 is yes, meaning that motor speed (RPM) type of backup therapy is to be provided, then the method proceeds to step 295. At step 295, ventilator 5 is caused to provide the appropriate motor speed (RPM) type backup therapy based upon the appropriate stored backup parameter(s). In the particular embodiment being described, the average flow generator speed during IPAP delivery over six breaths is used to set the speed of the flow generator 10 for the IPAP cycle and the average flow generator speed during EPAP delivery over six breaths is used to set the speed of the flow generator 10 for the EPAP cycle. In addition, if appropriate for the current mode of ventilator 5 (e.g., for S/T, T, PC, PC-SIMV, AC, CV and SIMV modes which are known in the art), the patient breath rate average over six breaths is used to determine how often IPAP/EPAP cycles are provided, and the patient inspiration time average over six breaths is used to set the breath length of the inspiratory phase. Thus, as will be appreciated, following steps 285 through 295, the patient will be provided with some form of backup therapy as a result of the generation of an alarm which indicates that, due to a hardware related problem, therapy cannot effectively be provided according to specification.

Following either step 290 or step 295, as appropriate, the method proceeds to step 300, wherein a determination is made as to whether at least one of the alarms is a ventilator inoperative (Vent Inop) type alarm. If the answer at step 300 is yes, then, at step 305, a determination is made as to whether the flow generator 10 has been turned off and then on. If the answer at step 305 is no, then the method returns to step 305. If the answer at step 305 is yes, then the method proceeds to step 310. Thus, as will be appreciated, steps 300 and 305 will result in the determined backup therapy being continuously provided until the flow generator 10 has been turned off and then on again. In other words, backup therapy in a case of a ventilator inoperative (Vent Inop) alarm cannot be terminated and shall remain in effect until the flow generator 10 is turned off. If the answer at step 300 is no, meaning that each of the one or more alarms is circuit check type alarm, then the method proceeds directly to step 310.

At step 310, a determination is made as to whether at least one alarm is still active. If the answer is no, then, at step 315, the ventilator resumes normal therapy as the condition that led to the one or more alarms has been rectified. Following step 315, the method returns to step 255. If, however, the answer at step 310 is yes, meaning that at least one alarm is still active, then the method proceeds to 320. At step 320, a determination is made as to whether at least one of the alarms is a newly generated alarm. If the answer is yes, then the method proceeds to step 285. If the answer is no at step 320, then the method returns to step 310.

Thus, as will be appreciated from the foregoing, the alarms that cause the ventilator 5 to provide motor speed (RPM) based backup therapy are checked first, and therefore this control type has priority over the backup therapy that is based upon pressure support and the associated alarms. This means that once pressure support type backup therapy is being delivered, the potential exists for backup therapy to automatically be switched to the motor speed (RPM) based backup therapy depending upon the occurrence of additional alarms. However, once motor speed (RPM) backup therapy is being delivered, the ventilator cannot automatically switch to pressure support based backup therapy.

In addition, as discussed briefly above, when backup therapy is delivered due to the occurrence of a ventilator inoperative (Vent Inop) alarm, the backup therapy (motor speed based or pressure support type) cannot be terminated (but can be automatically switched from pressure support type to motor speed based) and shall remain in effect until the flow generator 10 is turned off. However, when backup therapy is initiated due to only one or more circuit check type alarms, the backup therapy can be terminated or automatically switched from pressure support type to motor speed based) and normal therapy can be resumed once the alarm is no longer active.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of operating a ventilator having a flow generator, comprising:
   (a) storing a plurality of predetermined alarms that may be generated by the ventilator and for each of the predetermined alarms a type of backup therapy that is to be provided in an event of the predetermined alarm, wherein the type of backup therapy is either (i) a flow generator speed type ventilation therapy using a set flow generator speed or speeds or (ii) a pressure support type ventilation therapy using a set pressure level or levels, wherein for a first one or more of the predetermined alarms the type of backup therapy is the flow generator speed type ventilation therapy and for a second one or more of the predetermined alarms the type of backup therapy is the pressure support type ventilation therapy;
   (b) providing a specified ventilation therapy to a patient through the ventilator according to a specification;
   (c) determining and storing a number of first backup parameters comprising at least one average rotational speed of the flow generator calculated over a plurality of breaths while the specified ventilation therapy was being provided to the patient and a number of second backup parameters comprising at least one average pressure level delivered by the flow generator calculated over the plurality of breaths;
   (d) determining that an alarm condition exists, wherein the alarm condition indicates a problem with the ventilator that would prevent the ventilator from providing the specified ventilation therapy to the patient according to the specification;
   (e) responsive to determining that the alarm condition exists, determining whether the alarm condition is one of the first one or more of the predetermined alarms and responsive to determining that the alarm condition is one of the first one or more of the predetermined alarms, providing backup ventilation therapy to the patient through the ventilator in the form of flow generator speed type ventilation therapy using a set rotational speed or speeds of the flow generator determined based on the stored number of first backup parameters; and
   (f) responsive to determining that the alarm condition is not one of the first one or more of the predetermined alarms, providing backup ventilation therapy to the patient through the ventilator in the form of pressure support type ventilation therapy using a set pressure level or levels determined based on the stored number of second backup parameters.

2. The method according to claim 1, wherein step (c) further comprises determining and storing a number of third backup parameters including at least one of (i) a patient breath rate average over the plurality of breaths and (ii) a patient inspiration time average over the plurality of breaths, and wherein one or more parameters of the flow generator speed type ventilation therapy are determined based on at least one of the number of third backup parameters, and wherein one or more parameters of the pressure support type ventilation therapy are determined based on at least one of the number of third backup parameters.

3. The method according to claim 2, wherein one or more parameters of the flow generator speed type ventilation therapy are determined based on each of the number of third backup parameters, and wherein one or more parameters of the pressure support type ventilation therapy are determined based on each of the number of third backup parameters.

4. The method according to claim 1, wherein the number of first backup parameters includes an average generator speed during IPAP and an average generator speed during EPAP, and wherein the number of second backup parameters include an average IPAP level delivered to the patient and an average EPAP level delivered to the patient.

5. The method according to claim 4, wherein the providing backup ventilation therapy to the patient through the ventilator in the form of pressure support type ventilation therapy comprises using the average IPAP level to set a pressure level for the flow generator during an IPAP cycle and using the average EPAP level to set a pressure level for the flow generator during an EPAP cycle.

6. The method according to claim 4, wherein the providing backup ventilation therapy to the patient through the ventilator in the form of flow generator speed type ventilation therapy comprises using the average generator speed during IPAP to set a rotational speed for the flow generator during an IPAP cycle and using the average generator speed during EPAP to set a rotational speed for the flow generator during an EPAP cycle.

7. The method according to claim 1, further comprising determining whether each of the plurality of breaths is a valid breath, wherein the step of determining and storing the number of first backup parameters and the number of second backup parameters is performed only if each of the plurality of breaths is determined to be a valid breath.

8. The method according to claim 7, wherein the step of determining and storing the number of first backup parameters and the number of second backup parameters is repeated each time a new valid breath is taken by the patient such that the first and second backup parameters are re-determined and re-stored for a most recent in time of the plurality of breaths.

9. The method according to claim 1, wherein the alarm condition indicates a hardware problem with the ventilator that would prevent the ventilator from providing the specified ventilation therapy to the patient according to the specification.

10. The method according to claim 9, wherein the ventilator includes a sensor, and wherein the alarm condition indicates a problem with the sensor.

11. The method according to claim 9, wherein the ventilator comprises a patient circuit for transporting gas to and from the patient and wherein the alarm condition indicates a problem relating to the patient circuit.

12. The method according to claim 1, wherein the ventilator includes a first pressure sensor and a second pressure sensor, wherein the alarm condition indicates that both the first and the second pressure sensors have failed and is one of the first one or more of the predetermined alarms.

13. The method according to claim 1, wherein the ventilator includes a first flow sensor and a second flow sensor, wherein the alarm condition indicates that both the first and the second flow sensors have failed and is not one of the first one or more of the predetermined alarms, and wherein, responsive to the alarm condition indicating that both the first and the second flow sensors have failed, determining the backup ventilation therapy to be the pressure support type ventilation therapy.

14. The method according to claim 1, wherein step (f) comprises responsive to determining that the alarm condition is not one of the first one or more of the predetermined alarms, providing backup ventilation therapy to the patient through the ventilator in the form of pressure support type ventilation therapy using a set pressure level or levels determined based on the stored number of second backup parameters only if it is determined that the backup ventilation therapy in the form of flow generator speed type ventilation therapy is not currently being provided to the patient.

* * * * *